US008207381B2

(12) United States Patent
Hammond et al.

(10) Patent No.: US 8,207,381 B2
(45) Date of Patent: Jun. 26, 2012

(54) THERAPEUTIC COMPOUNDS

(75) Inventors: Gerald B. Hammond, Louisville, KY (US); Bo Xu, Louisville, KY (US); Paula J. Bates, Louisville, KY (US)

(73) Assignee: University of Louisville Research Foundation, Louisville, KY (US)

( * ) Notice: Subject to any disclaimer, the term of this patent is extended or adjusted under 35 U.S.C. 154(b) by 423 days.

(21) Appl. No.: 12/027,154

(22) Filed: Feb. 6, 2008

(65) Prior Publication Data

US 2008/0188570 A1 Aug. 7, 2008

Related U.S. Application Data

(60) Provisional application No. 60/899,788, filed on Feb. 6, 2007.

(51) Int. Cl.
*C07C 33/42* (2006.01)
*A61K 31/45* (2006.01)
(52) U.S. Cl. ............... 568/843; 514/739; 514/546
(58) Field of Classification Search ................. None
See application file for complete search history.

(56) References Cited

U.S. PATENT DOCUMENTS 6,387,901 B1    5/2002   Chupak

FOREIGN PATENT DOCUMENTS

DE           10029709 A1    1/2002

OTHER PUBLICATIONS

Goffin et al., DNA methyltransferase inhibitors-state of the art, 2002, Annals of Oncology, vol. 13, pp. 1699-1716.*
Andre et al., Oxalipalatin, Fluorouracil, and leucovorin as Adjuvant Treatment for Colon Cancer, 2004, New England Journal of Medicine, vol. 350, No. 23, pp. 2343-2351.*
Wahnon et al., Mechanism-based Inhibition of an Essential Bacterial Adenine DNA Methyltransferase: Rationally Designed Antibiotics, 2001, J. Am. Chem. Soc., vol. 123, No. 5, pp. 976-977.*
Lan et al., An Efficient Preparation of TIPS-Halofluoropropyane and its Applicaition to the Diastereoselective synthesis of Propargylic Fluorohydrins, 2000, J. Org. Chem., American Chemical Society, vol. 65, No. 13, pp. 4217-4221.*
Buck et al., Alkylatin of 1-alkynes in THF, 2001, Tehedron Letters, vol. 42, pp. 5825-5827.*
Jeon et al, Inhibitoinof bovine Plasma Amine Oxidase by 1,4-Diamino-2-butenes and -2-butynes, 2003, Bioorganic & Medicinal Chem., vol. 11, pp. 4631-4641.*
Xu et al., A new convenient synthesis of propargylic fluorohydrins and 2,5-diunsubsittuted furans form fluoropropargyl chloride, Mar. 31, 2006, J. Org. Chem, American Chemical Society, vol. 71, No. 9, pp. 3518-3521.*
Butler, Rachel et al., "Histone deacetylase inhibitors as therapeutics for polyglutamine disorders", *Nature Reviews: Neuroscience*, 784-796, 2006.

(Continued)

*Primary Examiner* — Yate K Cutliff
(74) *Attorney, Agent, or Firm* — Fish & Richardson P.C.

(57) ABSTRACT

The invention provides compounds of Formula (I):

$$R_1 \text{———} R_2 \quad (I)$$

wherein $R_1$ and $R_2$ have any of the values or specific values defined herein, as well as compositions comprising such compounds and therapeutic methods comprising the administration of such compounds.

36 Claims, 4 Drawing Sheets

OTHER PUBLICATIONS

Hammond, Gerald B., "Nucleophilic and electrophilic substitutions of difluoropropargyl bromides", *Journal of Fluorine Chemistry*, 127, 476-488, 2006.

Hong, Jiyoung A. et al., "An Efficient Synthesis of Difluoropropargyl Bromides", *Synthesis*, 5, 803-806, 2006.

Jose, Binoy et al., "Novel histone deacetylase inhibitors: cyclic tetrapeptide with trifluoromethyl and pentafluoroethyl ketones", *Bioorganic & Medicinal Chemistry Letters*, 14, 5343-5346, 2004.

Marson, Charles M., "Structure-activity relationships of aryloxyalkanoic acid hydroxyamides as potent inhibitors of histone deacetylase", *Bioorganic & Medicinal Chemistry Letters*, 17, 136-141 2007.

Rico, Isabelle et al., "Reactivity of the Perhalogenoalkanes $CF_2BrX$ (X = Cl, Br) with Nucleophiles. Part 4. Condensation with Carbanions", *Journal of the Chemical Society, Perkin Transactions I, Organic and Bio-organic Chemistry*, 4, 1063-1065, 1982.

Rodriquez, Manuela et al., "Total Synthesis, NMR Solution Structure, and Binding Model of the Potent Histone Deacetylase Inhibitor FR235222", *Angew, Chem. Int. Ed.*, 45, 423-427, 2006.

Shinji, Chihiro, "Design, synthesis, and evaluation of cyclic amide/imide-bearing hydroxamic acid derivatives as class-selective histone deacetylase (HDAC) inhibitors", *Bioorganic & Medicinal Chemistry*, 14, 7625-7651, 2006.

Bo Xu et al: An Efficient Synthesis of Diflluoropropargyl Bromides Synthesis, No. 5, 2006, pp. 803-806, scheme 3: 4a/.

Yves Bessard et al. "Ring Opening of gem-Dihalocyclopropanes: Novel Types of 1, 4 Elimination Reactions" Tetrahedron, vol. 46, No. 15, pp. 5230-5236, p. 5232: compound 9.

Youqian et al: Studies on Highly Steroselective Addition-Elimination Reactions of 3-(Methoycarbonyl)-2-halo-1, 3(Z)-dienes Journal of Organometallic Chemistry, vol. 72, 2007, pp. 5901-5904, p. 5901; compound 1.

Brian E. McCarry et al. "A Facile Synthesis of Muscimol" Tetrahedron Letters, vol. 22, No. 51, 1981, pp. 5153-5156, p. 5155; compound 7.

Bruce C. Hamper: "Regioselective Synthesis of 1-Methyl-3Hydroxy-5-perfluoroalkylpyrazoles by the Addition of Methylhydrazine to Perfluoroalkylacetylenic Esters" Journal of Fluorine Chemistry, vol. 48, 1990, pp. 123-131; p. 124; compound 1C.

C. Stephen Vizniowski et al: "Propargyl Chlorides as Sources for Cobal Stabilized gamma-Carbonyl Cations" Journal of Organometallic Chemistry, vol. 60, 1995, pp. 7496-7502; table 1.

Donald J. Burton et al. "Facile General route to Perfluoroalkyl Allenes" Tetrahedron Letters, vol. 31, No. 26, 1990, pp. 3699-3702; p. 3700.

Database Caplus(Online) Chemical Abstracts Service, Columbus, Ohio, US: LE COQ, Andre: "Synthesis and properties of 3,4-epoxy-1,1-dichloro-1—butene and trichlorotetrolaldehyde" retrieved from Database accession No. 70:77675; abstract & Annales De Chimie (Paris, France) {14}3(6), 529-41 Coden: Ancpac:, 1968.

Thomas Gillmann et al. : Convenient Synthesis of Methyl 2-Bromo- and 2-Iodo-2,3-Butadienoates Synthetic Communications, vol. 24, No. 15, 1994, pp. 2133-2138; p. 2135; compounds 4,5.

Database Caplus (online) Chemical Abstracts Service, Colombus, Ohio, US: Battioni, Jean P. et al: "3-Lithiopropargyl halides as alkynylatin reagents" Retrieved from STN Databes Accession No. 1969:450025 abstract & Bullentin De Las Societe Chimique de France, 3(3), 911-14 Coden: BSCFAS; 1969.

Benaim, et al: "Reactions of acetylene chlorohydrin with complex anions of molybdenum and manganese: formation of. eta.3-bonded .alpha.-methylenelactones" Journal of Organometallic Chemistry, vol. 165, No. 2, 1979, pp. C28-C32; abstract; compound 1.

Brillon D, et al. "Synthesis of 11-and 12-membered rings by direct cyclization method" Canadian Journal of Chemistry 1987 (Jan. 1987), pp. 43-55; schemes 1,2; abstract.

Gerald B. Hammond: "Nucleophilic and electrophilic substitutions of difluoropropargyl bromides" Journal of Fluorine Chemistry, vol. 127, No. 4-5, 2006, pp. 476-488.

Richard W. Fuller et al. "Isolation and Structure/Activity Features of Halomon/Activity Features of Halomon-Related Antitumor Monterpenes from the Red Alga Portieria hornemanni" Journal of Medicine of Chemistry, vol. 37, No. 25, 1994, pp. 4407-4411.

\* cited by examiner

THERAPEUTIC COMPOUNDS

PRIORITY OF INVENTION

This application claims priority under 35 U.S.C. 119(e) from U.S. Provisional Application No. 60/899,788, filed 6 Feb. 2007.

GOVERNMENT FUNDING

The invention described herein was made with government support under Grant Number CHE-0213502 awarded by the National Science Foundation. The United States Government has certain rights in the invention.

BACKGROUND OF THE INVENTION

Chemotherapy plays a major role in the management of cancer (e.g., breast cancer). For individuals with recurrent or metastatic disease, systemic chemotherapy is often the treatment of choice. Unfortunately, systemic chemotherapy is rarely curative. In addition, treatment with standard chemotherapy agents, such as cyclophosphamide, 5-FU, doxorubicin and paclitaxel, results in significant side effects and is rarely curative in cases of advanced disease. Consequently, breast cancer alone claims the lives of close to 41,000 women each year in the U.S. Therefore, there is a pressing need for new anticancer agents with unique activity and/or fewer side effects.

SUMMARY OF THE INVENTION

Certain embodiments of the present invention provide compounds that have anti-cancer activity. Accordingly in one embodiment the invention provides a compound Formula (I):

$$R_1 \equiv\!\equiv\!\equiv R_2 \quad (I)$$

wherein:

$R_1$ is carboxy, $(C_1-C_{20})$alkoxycarbonyl, $(C_2-C_{20})$alkenyloxycarbonyl, $(C_2-C_{20})$alkynyloxycarbonyl, $(C_1-C_{20})$alkyl, $(C_2-C_{20})$alkenyl, or $(C_2-C_{20})$alkynyl, which $(C_1-C_{20})$alkyl, $(C_2-C_{20})$alkenyl, or $(C_2-C_{20})$alkynyl, is substituted with one or more groups independently selected from halo, hydroxy, mercapto, $(C_1-C_{20})$alkoxy, $(C_2-C_{20})$alkenyloxy, $(C_2-C_{20})$alkynyloxy, aryloxy, heteroaryloxy, $(C_3-C_{20})$cycloalkyloxy, heterocyclyloxy, $(C_1-C_{20})$alkylthio, $(C_2-C_{20})$alkenylthio, $(C_2-C_{20})$alkynylthio, carboxy, $(C_1-C_{20})$alkoxycarbonyl, $(C_2-C_{20})$alkenyloxycarbonyl, $(C_2-C_{20})$alkynyloxycarbonyl, aryl, heteroaryl, cycloalkyl, heterocyclyl, $NR_aR_b$, $(C_2-C_{20})$alkynoyloxy, and arylcarbonyloxy;

$R_2$ is $CF_2Br$, $CFHBr$, $CF_2Cl$, $CFHCl$, $CFBr_2$, $CFCl_2$, $CBr_3$, $C(R_c)(R_d)Br$, $C(R_c)(R_d)Cl$, $CF(R_e)Br$, $CF_2I$, $CFHI$, $C(R_c)(R_d)I$, $CF(RF_e)I$ or $CCl_3$;

each $R_a$ and $R_b$ is independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, $(C_2-C_{20})$alkynyloxy, or aryl-$(C_1-C_{20})$alkoxycarbonyl;

each $R_c$ and $R_d$ is independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy; and $R_e$ is $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy;

wherein each aryl, heteroaryl, heterocyclyl, aryloxy, heteroaryloxy, arylcarbonyloxy or heteroarylcarbonyloxy of $R_1$ is optionally substituted with one or more groups independently selected from halo, hydroxy, nitro, cyano, trifluoromethyl, trifluoromethoxy, mercapto, carboxy, $(C_1-C_{20})$alkyl, $(C_2-C_{20})$alkenyl, $(C_2-C_{20})$alkynyl, $(C_1-C_{20})$alkoxy, $(C_2-C_{20})$alkenyloxy, $(C_2-C_{20})$alkynyloxy, $(C_1-C_{20})$alkylthio, $(C_2-C_{20})$alkenylthio, $(C_2-C_{20})$alkynylthio, $(C_1-C_{20})$alkoxycarbonyl, $(C_2-C_{20})$alkenyloxycarbonyl, $(C_2-C_{20})$alkynyloxycarbonyl, aryl, heteroaryl, aryl$(C_1-C_{20})$alkyl, heteroaryl$(C_1-C_{20})$alkyl, aryl$(C_2-C_{20})$alkenyl, aryl$(C_2-C_{20})$alkynyl, heteroaryl$(C_2-C_{20})$alkenyl, heteroaryl$(C_2-C_{20})$alkynyl, $(C_1-C_{20})$alkanoyloxy, $(C_2-C_{20})$alkenoyloxy, $(C_2-C_{20})$alkynoyloxy;

or a salt thereof.

In one embodiment of the invention the compound of Formula (I) is not 4-bromo-4,4-difluorobut-2-ynoic acid.

In one embodiment of the invention the compound of Formula (I) is not 6-bromo-6,6-difluoro-2-methylhex-4-yn-3-ol.

In one embodiment of the invention the compound of Formula (I) is not 1-bromo-1,1-difluoro-non-2-yn-4-ol.

The invention also provides a pharmaceutical composition comprising a compound of Formula (I), or a pharmaceutically acceptable salt thereof, and a pharmaceutically acceptable carrier.

The invention also provides a method for treating cancer in an animal comprising administering a compound of Formula (I) or a pharmaceutically acceptable salt thereof to the animal.

The invention also provides a method for treating a pathological condition or symptom in an animal wherein the activity of DNA methyltransferase 1 is implicated and inhibition of its action is desired comprising administering a compound of Formula (I) or a pharmaceutically acceptable salt thereof to the animal. Such conditions include myelodysplastic syndrome (MDS), leukemia, a solid tumor, schizophrenia, sickle cell disease, and lupus (SLE).

The invention also provides a method for inhibiting the activity of DNA methyltransferase 1 comprising contacting the DNA methyltransferase 1 with a compound of Formula (I) or a pharmaceutically acceptable salt thereof.

The invention also provides a method for treating a hemaglobinopathy, such as a thalassemia (e.g. beta-thalassemia) in an animal comprising administering a compound of Formula (I) or a pharmaceutically acceptable salt thereof to the animal.

The invention also provides a compound of Formula (I) or a pharmaceutically acceptable salt thereof for use in medical therapy.

The invention also provides the use of a compound of Formula (I) or a pharmaceutically acceptable salt thereof for the manufacture of a medicament for the treatment of cancer in an animal.

The invention also provides the use of a compound of Formula (I) or a pharmaceutically acceptable salt thereof for the manufacture of a medicament for treating a pathological condition or symptom in an animal wherein the activity of DNA methyltransferase 1 is implicated and inhibition of its action is desired.

The invention also provides the use of a compound of Formula (I) or a pharmaceutically acceptable salt thereof for the manufacture of a medicament for the treatment of a hemaglobinopathy, such as a thalassemia (e.g. beta-thalassemia) in an animal.

The invention also provides processes and intermediates disclosed herein that are useful for preparing compounds of Formula (I) or salts thereof.

DETAILED DESCRIPTION

The following definitions are used, unless otherwise described: halo is fluoro, chloro, bromo, or iodo. Alkyl, alkenyl, alkynyl, alkoxy, alkenyloxy, alkynyloxy, alkylthio, etc., denote both straight and branched groups; but reference to an individual radical such as propyl embraces only the straight chain radical, a branched chain isomer such as isopropyl being specifically referred to. The term cycloalkyl includes monocyclic or polycyclic alkyl rings containing from 3 to 12 carbon atoms. The term alkenyl includes hydrocarbon chains that include one or more (e.g. 1, 2, 3, or 4) double bonds in the chain. The term alkynyl includes hydrocarbon chains that include one or more (e.g. 1, 2, 3, or 4) triple bonds in the chain, and that also may optionally include one or more (e.g. 1, 2, 3, or 4) double bonds in the chain. The number of carbons in a hydrocarbon chain (e.g. alkyl, alkenyl, or alkynyl) may be designated herein, for example, by ($C_1$-$C_{20}$), which means a chain comprising from 1 to 20 carbon atoms, or by another similar designation.

Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent, or is H, O, ($C_1$-$C_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "heterocyclyl" refers to a saturated, or partially unsaturated monocyclic radical containing 4-7 atoms and at least 1 heteroatom selected from the group consisting of oxygen, sulfur, and nitrogen N(Y), wherein Y is a point of attachment, H, O, ($C_1$-$C_4$)alkyl, phenyl or benzyl, as well as a radical of a bicyclic or tricyclic ring system derived therefrom, particularly, one derived by fusing a propylene, trimethylene, or tetramethylene diradical thereto, or one derived by fusing an aryl (e.g. a benz-group) or heteroaryl ring thereto.

As used herein the term "arylcarbonyloxy" means a group of the formula aryl-C(=O)—O—, wherein aryl has the meaning described hereinabove.

As used herein the term "heteroarylcarbonyloxy" means a group of the formula heteroaryl-C(=O)—O—, wherein heteroaryl has the meaning described hereinabove.

As used herein the term "aryloxycarbonyl" means a group of the formula aryl-O—C(=O)—, wherein aryl has the meaning described hereinabove.

As used herein the term "heteroaryloxycarbonyl" means a group of the formula heteroaryl-O—C(=O)—, wherein heteroaryl has the meaning described hereinabove.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-cancer activity using the standard tests described herein, or using other similar tests which are well known in the art.

Specific values listed below for radicals, substituents, and ranges are for illustration only; they do not exclude other defined values or other values within defined ranges for the radicals and substituents.

Specifically, ($C_1$-$C_{20}$)alkyl can be methyl, ethyl, propyl, isoproproyl, butyl, isobutyl, tertbutyl, pentyl, 3-pentyl, 2,2-dimethylprop-1-yl, hexyl, heptyl, octyl, nonyl, or decyl, etc.; ($C_1$-$C_{20}$)alkanoyl can be acetyl, propanoyl or butanoyl, etc.; ($C_1$-$C_{20}$)alkoxy can be methoxy, ethoxy, propoxy, isopropoxy, butoxy, pentoxy, or hexyloxy; ($C_1$-$C_{20}$)alkylthio can be methylthio, ethylthio, propylthio, isopropylthio, butylthio, isobutylthio, pentylthio, or hexylthio; ($C_2$-$C_{20}$)alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl, etc.; ($C_2$-$C_{20}$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl, etc.; ($C_1$-$C_{20}$)alkanoyl can be acetyl, propanoyl or butanoyl, etc.; ($C_1$-$C_{20}$)alkoxycarbonyl can be methoxycarbonyl, ethoxycarbonyl, propoxycarbonyl, isopropoxycarbonyl, butoxycarbonyl, tertbutoxycarbonyl, pentoxycarbonyl, or hexyloxycarbonyl, etc.; ($C_1$-$C_{20}$)alkanoyloxy can be acetoxy, propanoyloxy, butanoyloxy, isobutanoyloxy, tertbutanoyloxy, pentanoyloxy, or hexanoyloxy, etc.; aryl can be phenyl, indenyl, or naphthyl; heterocycle can be morpholinyl, piperazinyl, piperidinyl, pyrrolidinyl, tetrahydropyranyl, tetrahydrofuranyl, 1,4-dioxanyl, tetrahydropyridinyl, thiomorpholinyl, azetidinyl, aziridinyl, dihydroisoindoyl, 1,3-dioxolane or dihydroisoquinolinyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R_1$ is carboxy.

A specific value for $R_1$ is ($C_1$-$C_{20}$)alkoxycarbonyl, ($C_2$-$C_{20}$)alkenyloxy-carbonyl, or ($C_2$-$C_{20}$)alkynyloxycarbonyl.

A specific value for $R_1$ is ($C_1$-$C_{20}$)alkyl, ($C_2$-$C_{20}$)alkenyl, or ($C_2$-$C_{20}$)alkynyl, which ($C_1$-$C_{20}$)alkyl, ($C_2$-$C_{20}$)alkenyl, or ($C_2$-$C_{20}$)alkynyl, is substituted with one or more groups independently selected from carboxy, ($C_1$-$C_{20}$)alkoxycarbonyl, ($C_2$-$C_{20}$)alkenyloxycarbonyl, and ($C_2$-$C_{20}$)alkynyloxycarbonyl, and which ($C_1$-$C_{20}$)alkyl, ($C_2$-$C_{20}$)alkenyl, or ($C_2$-$C_{20}$)alkynyl is optionally substituted with one or more groups independently selected from halo, hydroxy, mercapto, ($C_1$-$C_{20}$)alkoxy, ($C_2$-$C_{20}$)alkenyloxy, ($C_2$-$C_{20}$)alkynyloxy, ($C_1$-$C_{20}$)alkylthio, ($C_2$-$C_{20}$)alkenylthio, ($C_2$-$C_{20}$)alkynylthio, aryl, heteroaryl, and $NR_aR_b$.

A specific value for R₁ is $(C_1-C_{20})$alkyl, $(C_2-C_{20})$alkenyl, or $(C_2-C_{20})$alkynyl, which $(C_1-C_{20})$alkyl, $(C_2-C_{20})$alkenyl, or $(C_2-C_{20})$alkynyl, is substituted with one or more groups independently selected from carboxy, $(C_1-C_{20})$alkoxycarbonyl, $(C_2-C_{20})$alkenyloxycarbonyl, and $(C_2-C_{20})$alkynyloxycarbonyl.

A specific value for R₁ is $(C_1-C_{20})$alkyl, $(C_2-C_{20})$alkenyl, or $(C_2-C_{20})$alkynyl, which $(C_1-C_{20})$alkyl, $(C_2-C_{20})$alkenyl, or $(C_2-C_{20})$alkynyl, is substituted with one or more carboxy.

A specific value for R₁ is $(C_1-C_{10})$alkyl, which $(C_1-C_{10})$ alkyl is substituted with one or more groups independently selected from carboxy, $(C_1-C_{20})$alkoxycarbonyl, $(C_2-C_{20})$ alkenyloxycarbonyl, and $(C_2-C_{20})$alkynyloxycarbonyl.

A specific value for R₁ is $(C_1-C_{10})$alkyl, which $(C_1-C_{10})$ alkyl is substituted with one or more carboxy.

A specific value for R₁ is $(C_1-C_{20})$alkyl, $(C_2-C_{20})$alkenyl, or $(C_2-C_{20})$alkynyl, which $(C_1-C_{20})$alkyl, $(C_2-C_{20})$alkenyl, or $(C_2-C_{20})$alkynyl, is substituted with one or more groups independently selected from halo, hydroxy, mercapto, $(C_1-C_{20})$ alkoxy, $(C_2-C_{20})$alkenyloxy, $(C_2-C_{20})$alkynyloxy, $(C_1-C_{20})$ alkylthio, $(C_2-C_{20})$alkenylthio, $(C_2-C_{20})$alkynylthio, carboxy, $(C_1-C_{20})$alkoxycarbonyl, $(C_2-C_{20})$alkenyloxycarbonyl, $(C_2-C_{20})$alkynyloxycarbonyl, aryl, heteroaryl, and $NR_aR_b$.

A specific value for R₁ is $(C_1-C_{20})$alkyl, $(C_2-C_{20})$alkenyl, or $(C_2-C_{20})$alkynyl, which $(C_1-C_{20})$alkyl, $(C_2-C_{20})$alkenyl, or $(C_2-C_{20})$alkynyl is substituted with hydroxy, mercapto, carboxy or $NR_aR_b$.

A specific value for R₁ is $(C_1-C_{20})$alkyl, $(C_2-C_{20})$alkenyl, or $(C_2-C_{20})$alkynyl, which $(C_1-C_{20})$alkyl, $(C_2-C_{20})$alkenyl, or $(C_2-C_{20})$alkynyl is substituted with hydroxy.

A specific value for R₁ is $(C_1-C_{20})$alkyl, $(C_2-C_{20})$alkenyl, or $(C_2-C_{20})$alkynyl, which $(C_1-C_{20})$alkyl, $(C_2-C_{20})$alkenyl, or $(C_2-C_{20})$alkynyl is substituted on the carbon adjacent to the triple bond in Formula (I) with hydroxy.

A specific value for R₁ is a $(C_5-C_{10})$alkyl, $(C_2-C_{10})$alkenyl, or $(C_2-C_{10})$alkynyl that is substituted with hydroxy, mercapto, carboxy or $NR_aR_b$.

A specific value for R₁ is a $(C_5-C_{10})$alkyl, $(C_2-C_{10})$alkenyl, or $(C_2-C_{10})$alkynyl that is substituted with hydroxy.

A specific value for R₁ is a $(C_5-C_{10})$alkyl, $(C_2-C_{10})$alkenyl, or $(C_2-C_{10})$alkynyl that is substituted on the carbon adjacent to the triple bond in Formula (I) with hydroxy.

A specific value for R₁ is a $(C_5-C_{10})$alkyl that is substituted with hydroxy, mercapto, carboxy or $NR_aR_b$.

A specific value for R₁ is a $(C_5-C_{10})$alkyl that is substituted with hydroxy.

A specific value for R₁ is a $(C_5-C_{10})$alkyl that is substituted on the carbon adjacent to the triple bond in Formula (I) with hydroxy.

A specific value for R₁ is 2,2-dimethyl1-hydroxyprop-1-yl, 1-hydroxyhept-4-ene-1-yl, 2-ethyl-1-hydroxyhex-1-yl, 3-phenyl-1-hydroxyprop-1-yl, 1-hydroxy-hex-1-yl, R-1-hydroxy-hex-1-yl, S-1-hydroxy-hex-1-yl, carboxy, 1-bromo-hex-1-yl, 1-benzoyloxyhex-1-yl, 1-acetoxyhex-1-yl, 1-phenoxyhex-1-yl, 1-hydroxy-but-1-yl, 1-hydroxyoct-1-yl, 1-hydroxy-1-dec-1-yl, 1-hydroxy-1-dodec-1-yl, 1-Cyclopropyl-1-hydroxymethyl, 1-cyclohexyl-1-hydroxymethyl, 1-hydroxy-2,4-hexadiene-1-yl, 2-ethyl-1-hydroxyhex-1-yl, 2-methyl-1-hydroxypent-1-yl, 3-[N-(benzyloxycarbonyl)amino]-1-hydroxyprop-1-yl, or A specific value for R₁ is 1-hydroxyhex-3-ene-1-yl.

A specific value for R₂ is $CF_2Br$, $CFHBr$, $CF_2Cl$, or $CFHCl$.

A specific value for R₂ is $CF_2Br$.

A specific compound of formula (I) is a compound of formula (II):

(II)

wherein: R₃ is hydroxy, mercapto, chloro, bromo, methylthio, ethylthio, methoxy, ethoxy, or acetylamino; and R₄ is $(C_4-C_{10})$alkyl, $(C_2-C_{10})$alkenyl, or $(C_2-C_{10})$alkynyl, which $(C_4-C_{10})$alkyl, $(C_2-C_{10})$alkenyl, or $(C_2-C_{10})$alkynyl is optionally substituted with one or more groups independently selected from halo, hydroxy, mercapto, $(C_1-C_{10})$alkoxy, $(C_1-C_{10})$ alkylthio, carboxy, $(C_1-C_{10})$alkoxycarbonyl, aryl, heteroaryl, and $NR_aR_b$. A specific value for R₄ is $(C_4-C_{10})$alkyl that is optionally substituted with one or more groups independently selected from halo, hydroxy, mercapto, $(C_1-C_{10})$alkoxy, $(C_1-C_{10})$alkylthio, carboxy, $(C_1-C_{10})$alkoxycarbonyl, aryl, heteroaryl, and $NR_aR_b$.

A specific compound of the invention is a compound of formula (I):

(I)

wherein: R₁ is carboxy, $(C_1-C_{20})$alkoxycarbonyl, $(C_2-C_{20})$ alkenyloxycarbonyl, $(C_2-C_{20})$alkynyloxycarbonyl, $(C_1-C_{20})$ alkyl, $(C_2-C_{20})$alkenyl, or $(C_2-C_{20})$alkynyl, which $(C_1-C_{20})$ alkyl, $(C_2-C_{20})$alkenyl, or $(C_2-C_{20})$alkynyl, is substituted with one or more groups independently selected from halo, hydroxy, mercapto, $(C_1-C_{20})$alkoxy, $(C_2-C_{20})$alkenyloxy, $(C_2-C_{20})$alkynyloxy, $(C_1-C_{20})$alkylthio, $(C_2-C_{20})$alkenylthio, $(C_2-C_{20})$alkynylthio, carboxy, $(C_1-C_{20})$alkoxycarbonyl, $(C_2-C_{20})$alkenyloxycarbonyl, $(C_2-C_{20})$alkynyloxycarbonyl, aryl, heteroaryl, and $NR_aR_b$;

R₂ is $CF_2Br$, $CFHBr$, $CF_2Cl$, $CFHCl$, $CFBr_2$, $CFCl_2$, $CBr_3$, $C(R_c)(R_d)Br$, $C(R_c)(R_d)Cl$, $CF(R_e)Br$, or $CCl_3$;

each $R_a$ and $R_b$ is independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy;

each $R_c$, and $R_d$ is independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy; and $R_e$ is $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy;

wherein each aryl or heteroaryl of R₁ is optionally substituted with one or more groups independently selected from halo, hydroxy, nitro, cyano, trifluoromethyl, trifluoromethoxy, mercapto, carboxy, $(C_1-C_{20})$alkyl, $(C_2-C_{20})$alkenyl, $(C_2-C_{20})$alkynyl, $(C_1-C_{20})$alkoxy, $(C_2-C_{20})$alkenyloxy, $(C_2-C_{20})$alkynyloxy, $(C_1-C_{20})$alkylthio, $(C_2-C_{20})$alkenylthio, $(C_2-C_{20})$alkynylthio, $(C_1-C_{20})$alkoxycarbonyl, $(C_2-C_{20})$alkenyloxycarbonyl, $(C_2-C_{20})$alkynyloxycarbonyl, aryl, heteroaryl, aryl$(C_1-C_{20})$alkyl, heteroaryl$(C_1-C_{20})$alkyl, aryl$(C_2-C_{20})$alkenyl, aryl$(C_2-C_{20})$alkynyl, heteroaryl$(C_2-C_{20})$alkenyl, heteroaryl$(C_2-C_{20})$alkynyl, $(C_1-C_{20})$alkanoyloxy, $(C_2-C_{20})$alkenoyloxy, $(C_2-C_{20})$alkynoyloxy;

or a pharmaceutically acceptable salt thereof.

A specific value for $R_4$ is $(C_4-C_{10})$alkyl that is optionally substituted with one or more groups independently selected from halo, hydroxy, mercapto, carboxy, $(C_1-C_{10})$alkoxycarbonyl, and $NR_aR_b$.

A specific value for $R_4$ is $(C_4-C_{10})$alkyl.

A specific value for $R_4$ is $(C_4-C_6)$alkyl.

A specific compound of Formula (I) is 1-bromo-1,1-difluoro-4-hydroxy-2-nonyne or 1-bromo-1,1-difluoro-4-hydroxy-5,5-dimethyl-2-hexyne, or a salt thereof.

A specific compound of Formula (I) is or a salt thereof.

Processes for preparing compounds of Formula (I) or salts thereof are provided as further embodiments of the invention and are illustrated by the following procedures in which the meanings of the generic radicals are as given above unless otherwise qualified.

A compound of Formula (I) can be prepared by reacting a deprotonated terminal alkyne of formula 1 with an electrophile of formula 2 wherein X is a suitable leaving group. The terminal alkyne may include one or more other functional groups or protected functional groups.

As illustrated below, a compound of Formula (I) wherein $R_1$ is a $(C_1-C_{20})$alkyl that is substituted on the carbon adjacent to the triple bond in Formula (I) with hydroxy, and that is optionally further substituted with one or more groups can be prepared by reacting a trialkylsilyl alkyne of formula 3 with an aldehyde of formula 4 to provide the corresponding compound of Formula (I).

The reaction can conveniently be carried out by treating the compound of formula 3 with the aldehyde 4 and a fluoride ion source (e.g., tetrabutylammonium fluoride) in a suitable solvent.

The compound of formula 5 can be further modified to provide other compounds of Formula (I), such as compounds of formula 6-8, as illustrated below.

Conversion of an alcohol of formula 5, for example by bromination with $CBr_4$ and triphenylphosphine, provides a bromide of formula 6. Treatment of an alcohol of formula 5 with diethyl azodicarboxylate (DEAD), triphenylphosphine, and a thiol of formula RSH provides a sulfide of formula 7. Treatment of an alcohol of formula 5, with diethyl azodicarboxylate, triphenylphosphine, and an amide (e.g., of formula $CH_3CONH_2$) provides an amide of formula 8.

Compound 9 below was first reported in the literature (*Journal of the Chemical Society, Perkin Transactions* 1:1063-5; 1982). As illustrated below, it can also be prepared as described by G. B. Hammond *J. Fluorine Chem.* 2006, 127, 476-488.

Compounds of Formula (I) wherein $R_1$ is an alkyl, alkenyl, or alkynyl group that is substituted with a carboxy group can be prepared by reacting the corresponding alkynyl lithium with dibromodifluoromethane.

A compound of Formula (II) wherein $R_3$ is hydroxy and $R_2$ is $CH_2Br$ can be prepared as illustrated below.

PG = protecting group such as dihydropyranyl

Intermediates of formulae 1-4 are particularly useful for preparing compounds of Formula (I).

In cases where compounds are sufficiently basic or acidic, a salt of a compound of Formula (I) can be useful as an intermediate for isolating or purifying a compound of Formula (I). Additionally, administration of a compound of Formula (I) as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of Formula (I) can be formulated as pharmaceutical compositions and administered to a mammalian host, such as a human patient, in a variety of forms adapted to the chosen route of administration, e.g., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the appropriate solvent with various of the other ingredients enumerated above, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically-acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of Formula (I) to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of Formula (I) can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of Formula (I) in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, effective for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound can be conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for the treatment of cancer. Examples of such agents include alkylating agents (e.g. carmustine, chlorambucil, cisplatin, lomustine, cyclophosphamide, melphalan, mechlorethamine, procarbazine, thiotepa, uracil mustard, triethylenemelamine, busulfan, pipobroman, streptozocin, ifosfamide, dacarbazine, carboplatin, and hexamethylmelamine), antimetabolites (e.g. cytosine arabinoside, fluorouracil, gemcitabine, hydroxyurea, mercaptopurine, methotrexate, azaserine, thioguanine, floxuridine, fludarabine, cladribine and L-asparaginase), natural products (e.g. actinomycin D, bleomycin, camptothecins, daunomycin, doxorubicin, etoposide, mitomycin C, (paclitaxel), taxotere, teniposide, vincristine, vinorelbine, mithramycin, idarubicin, (plicamycin), and deoxycoformycin), hormonal agents (e.g. tamoxifen), and other agents (e.g. mitotane, mitoxantrone, vinblastine, and levamisole).

In a specific embodiment of the invention, the compound can be administered or formulated in combination with one or more other DNMT inhibitors (e.g. dacitabine).

In a specific embodiment of the invention, the compound can be administered or formulated in combination with one or more HDAC inhibitors (e.g. vorinostat).

In a specific embodiment of the invention, the compound can be administered or formulated in combination with one or more other therapeutic agents (e.g. sorafenib, sutent, herceptin, avastatin, gleevec, iressa, or tarceva).

Accordingly, in one embodiment the invention also provides a composition comprising a compound of Formula (I), or a pharmaceutically acceptable salt thereof, at least one other therapeutic agent, and a pharmaceutically acceptable diluent or carrier. The invention also provides a kit comprising a compound of Formula (I), or a pharmaceutically acceptable salt thereof, at least one other therapeutic agent, packaging material, and instructions for administering the compound of Formula (I) or the pharmaceutically acceptable salt thereof and the other therapeutic agent or agents to an animal to treat a condition (e.g. cancer).

The ability of a compound of the invention to act as an anticancer agent may be determined using pharmacological models which are well known to the art, or using Test A described below.

Test A.

A test compound is suspended in sterile water or DMSO and diluted with sterile water to appropriate concentrations (final DMSO will be <0.5%). Samples are added to MDA-MB-231 and MCF7 breast cancer cells plated in 96 well plates to give final concentrations of $10^{-10}$, $10^{-9}$, $10^{-8}$, $10^{-7}$, $10^{-6}$ M in triplicate wells. Each plate contains a positive control and a negative control (untreated cells). Cells are incubated for 4 days and proliferation is measured using the colorimetric MTT (3-(4,5-dimethylthiazol-2-yl)-2,5-diphenyltetrazolium bromide) assay (see *Methods Mol Biol* 1998, 79, 79-83). Representative compounds of Formula (I) were tested in this assay and were found to have useful activity.

The ability of a compound of the invention to act as an inhibitor of DNMT1 may be determined using pharmacological models which are well known to the art, or using Test B described below.

Test B In Vitro Enzyme Assay Using recombinant Human DNMT1

A method similar to that described by Carcinogenesis, 2006, 27, 269-77 can be used to evaluate the ability of a compound to act as an inhibitor of DNMT1. Briefly, compounds are incubated with recombinant human DNMT1 (which is commercially available), hemimethylated DNA substrate (poly[dI-dC]) and S-adenosyl-[methyl-$^3$H]-methionine as a methyl donor. After the reaction, DNA is precipitated and incorporated $^3$H is measured. Caffeic acid at 20 $\mu$M is used as a positive control.

The ability of a compound of the invention to affect DNA methylation in cultured cells may be determined using pharmacological models which are well known to the art, or using Test C described below.

Test C Effects on Promoter Methylation and Gene Expression in Breast Cancer Cells Genes that are known to be regulated by promoter methylation in breast cancer cells, including estrogen receptor RASS1FA and CDKN2A are evaluated. RT-PCR and western blotting analyses is carried out for these gene products using extracts from MCF7 and MDA-MB-231 breast cancer cells that have been treated with varying doses of a compound of Formula (I). Expression is examined at several time points and 5-azacytidine is used as a positive control. Methylation specific PCR is used to confirm that activity is due to demethylation of the relevant promoter. Briefly, genomic DNA is treated with sodium bisulfate, which converts unmethylated cytosines to uracil. Complementary PCR primers will therefore require A to recognize uracil (from unmethylated cytosines), but G to recognize methylated cytosines. A nested PCR protocol can thus distinguish between methylated and unmethylated promoters.

Test D Anti-Cancer Activity

The compound of Example 1 below was screened against a panel of 60 human tumor cell lines. This screening revealed that the compound was potent and that the compound had a distinctive pattern of activity. The compound was highly active in breast, prostate, colon and brain (CNS) tumor cells, but less potent in other tumor types, e.g. melanomas. One of the most sensitive cell types was breast cancer, with all seven of the cell lines (including a doxorubicin-resistant line) having $GI_{50}$ values in the 10-66 nM range.

Figures 1, 1A, 1B:
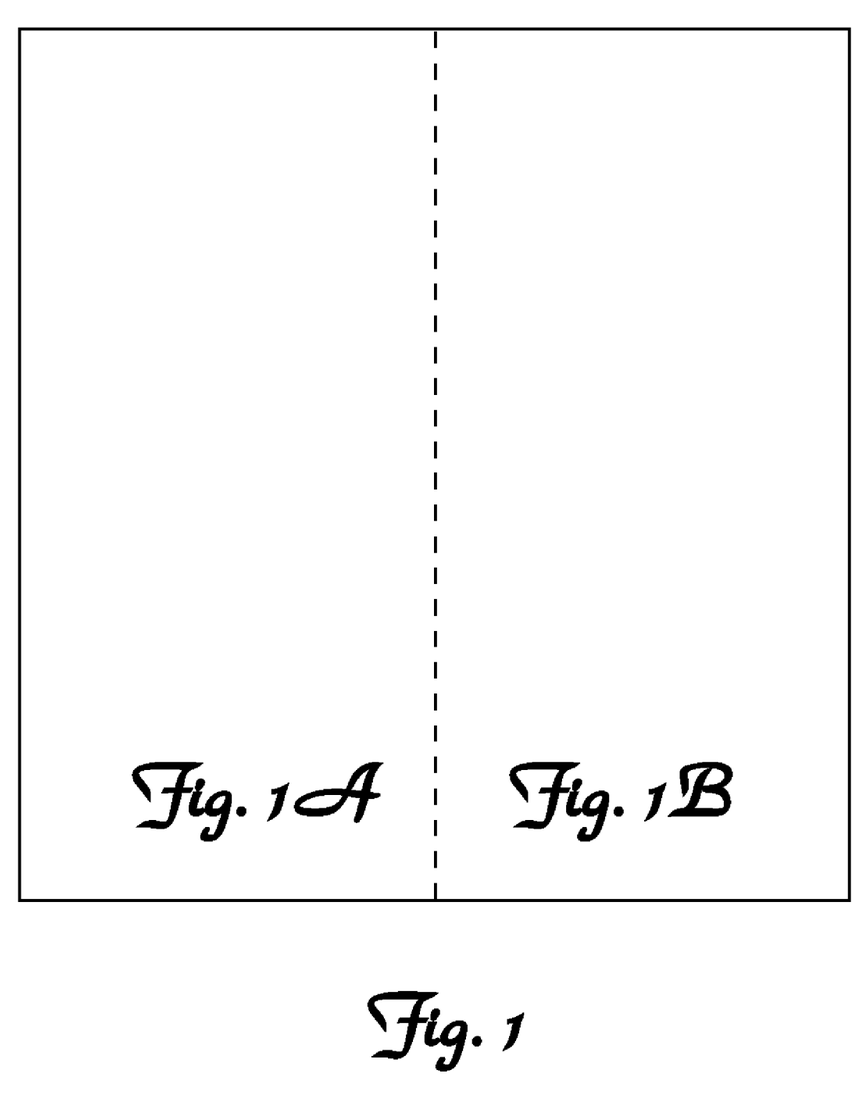
FIG. 1. Illustrates Mean Graph Representations showing the activity profiles of the compound of Example 1, FIG. 1A and Halomon FIG. 1B in the 60 Tumor Cell Line Screen.
Figure 1A:
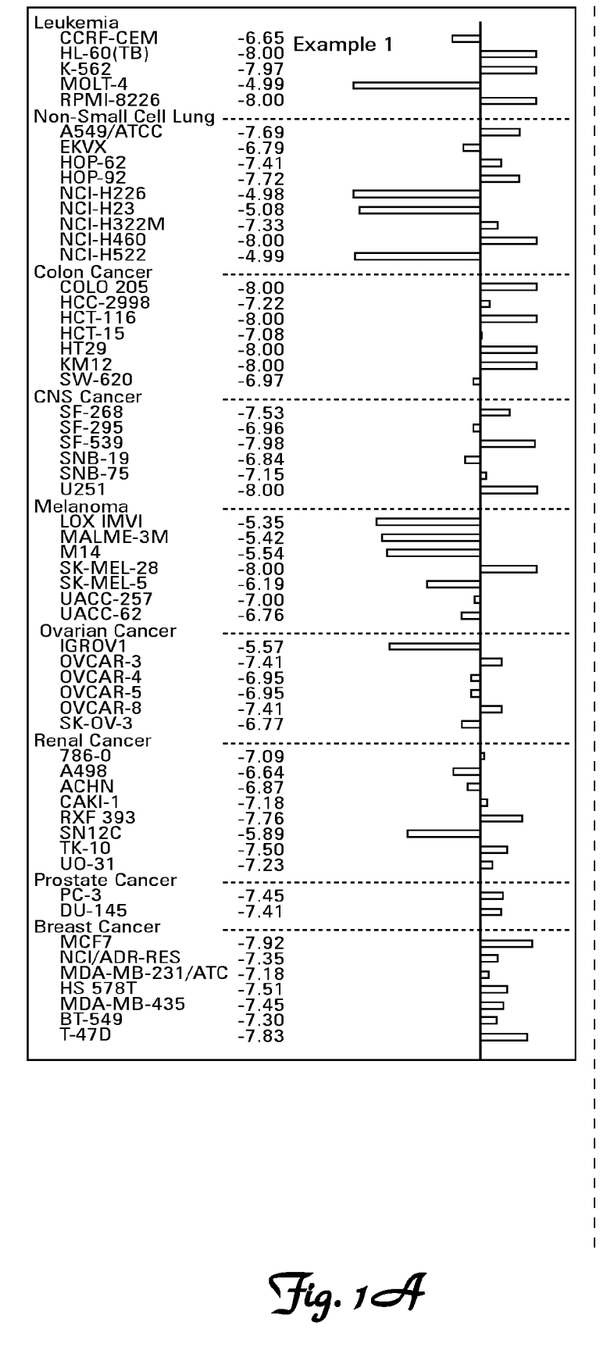
Figure 1B:
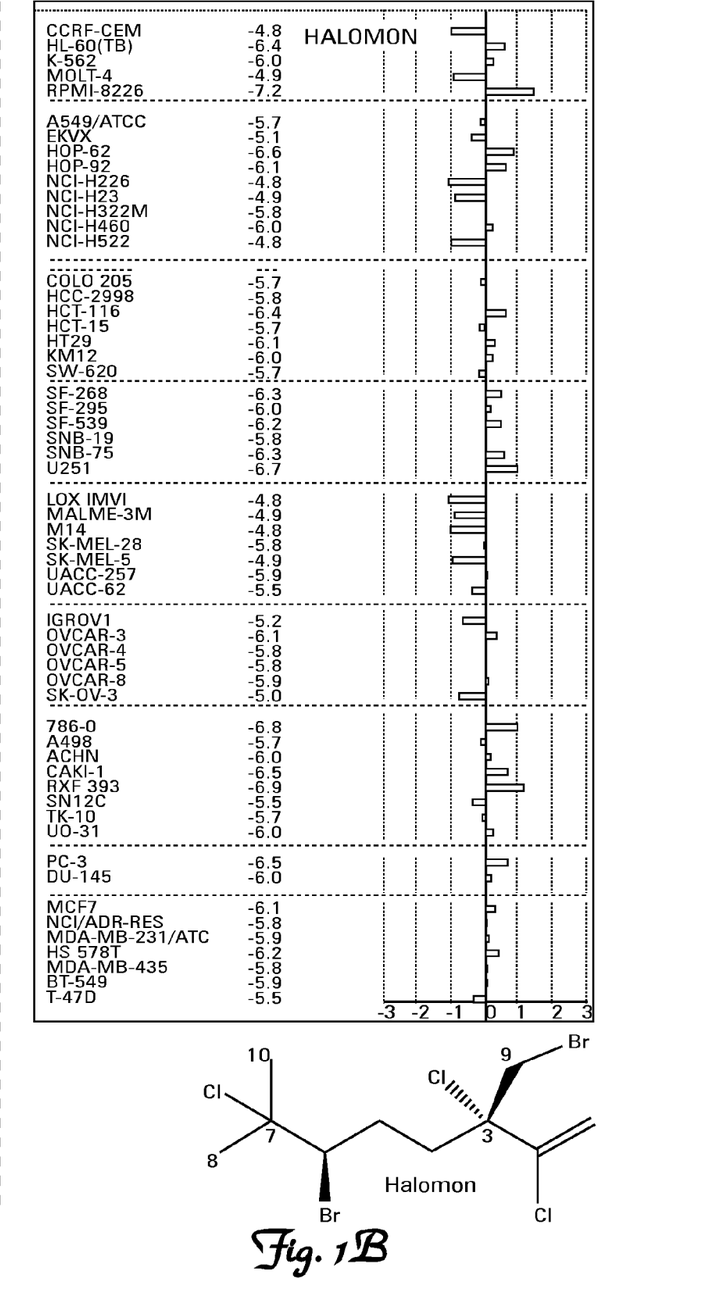

Analysis of the 60 cell line data using the on-line COMPARE program, which allows comparison of the activity profile of a "seed" with the more than 60,000 compounds in the public database, was also carried out. When the compound of Example 1 was used as a COMPARE seed, a strong correlation (Pearson coefficient 0.82) with a compound known as halomon was found. Halomon is a halogenated monoterpene that is structurally distinct from the compound of Example 1. Nonetheless, similarity for certain tumor types (e.g. breast, colon, CNS) and for specific cell lines within each panel was found. These results suggest that the compound of Example 1 and halomon share the same mechanism of action. Mean Graph Representations showing the activity profiles of the compound of Example 1 and Halomon (right panel) in the 60 Tumor Cell Line Screen are shown in FIG. 1.

Test E The Methyltransferase Activity of the Compound of Example 1 was Evaluated as Follows.

For experiments 1 and 2, A549 non-small cell lung cancer cells were incubated with the compound of Example 1 (1 μM final concentration) or vehicle (untreated) for 2 h and nuclear extracts were prepared by standard methods. The total DNA methyltransferase activity of the extracts was measured using EpiQuik™ DNA Methyltransferase Activity/Inhibition Assay Kit (Epigentek, Brooklyn, N.Y.), according to the manufacturer's directions. For experiment 3, the assay was carried out using purified HeLa nuclear extracts in the presence of the compound of Example 1 (500 nM final concentration) or vehicle (untreated).

The assay involves incubation of nuclear extracts (as a source of DNA methyltransferase activity) with immobilized DNA substrate in the presence of Adomet (methyl donor). The DNA methyltransferase activity was measured by determining levels of 5-methylcytosine in the DNA substrate using a primary antibody to 5-methylcytosine and a secondary antibody for colorimetric detection at 450 nm. Results are presented in the following table.

TABLE

| | Relative DNA Methyltransferase Activity | | |
|---|---|---|---|
| Experiment | 1. Using nuclear extracts from untreated or Example 1 treated (1 μM for 2 h) lung cancer cells. | 2. Repeat experiment using nuclear extracts from untreated or Example 1 treated (1 μM for 2 h) lung cancer cells. | 3. Using 20 μg of HeLa nuclear extracts incubated in vitro with 500 nM Example 1 |
| Untreated | 0.114 | 0.122 | 0.264 |
| Example 1-treated | 0.073 | 0.075 | 0.092 |

Test F In-Vivo Effects of Compound of Example 1.

The following study was designed to assess toxicity and activity in female nude mice bearing A549 human non-small cell lung cancer xenografts. Athymic nude mice were inoculated subcutaneously (s.c.) with A549 cells and treatment began after small tumors were visible. The compound of Example 1 was prepared at 100 mg/ml or 50 mg/ml in DMSO and diluted 1:10 with sterile PBS. Mice were treated by intraperitoneal (i.p.) injections of 100 μl of these solutions, equivalent to approximately 25 mg/kg or 50 mg/kg; the control group received identical injections of vehicle (10% DMSO in PBS). Mice received injections of the compound of Example 1 or vehicle five times per week (once per day, except on weekends) for up to 30 injections. There was no evidence of acute toxicity in mice treated with the compound of Example 1, as judged by body weight and behavior of the mice The tumors grew slower in the treated mice compared to control-treated mice, although the difference was not statistically significant (see A in FIG. 2). Evaluating the long-term outcome was complicated by the fact that several animals in the compound of Example 1 treated groups developed tumor necrosis/ulceration and had to be euthanized before the end of the experiment, as required by IACUC protocol. This tumor necrosis is believed to be treatment-related as it occurred in 5/12 treated animals, but 0/6 of the control group. There was suggestion that the observed tumor necrosis was predictive of an anti-tumor effect, because the size of the ulcerated tumors was substantially smaller than those in the control group at the same time point (see B in FIG. 2). The overall response seemed to be equivalent or better in the low dose group compared with the high dose group, but that may be consistent with the mechanism of action, since a similar effect has been observed for decitabine in humans. These in vivo results show that the compound of Example 1 exhibits no evidence of acute toxicity and suggesting it can induce tumor necrosis in a mouse model of cancer.

The invention will now be illustrated by the following non-limiting Examples.

EXAMPLE 1

Synthesis of 1-bromo-1,1-difluoro-non-2-yn-4-ol

To a solution of (3-bromo-3,3-difluoro-prop-1-ynyl)-triisopropyl-silane (156 mg, 0.5 mmol) and hexanal (60 mg, 0.6 mmol) in THF (5 mL), TBAF (1M, 0.75 mL) was added dropwise at −90° C. After the addition was completed, the reaction mixture was stirred for 0.5 h and quenched with saturated aq. NH$_4$Cl. The mixture was extracted with ether (20 mL×3) and washed with water (20 mL×2). After drying over Na$_2$SO$_4$ the solvent was removed and the product was purified by silica gel chromatography (AcOEt:hexane=1:20) to afford the title compound (82 mg, 65%) as colorless liquid. Colorless liquid, yield: 78%. IR (neat): 3320, 2934, 2261, 1223, 1096 cm−1. 1H NMR (500 MHz, CDCl3) δ 4.49-4.52 (m, 1H), 2.14 (bs, 1H), 1.74-1.77 (m, 2H), 1.45-1.47 (m, 2H), 1.33-1.38 (m, 4H), 0.91 (t, J=6.5 Hz, 3H); 19F NMR (470 MHz, CDCl3) δ −32.9 (s, 2F); 13C NMR (125 MHz, CDCl3) δ 101.5 (t, J=288 Hz), 91.5 (t, J=5.8 Hz), 77.3 (t, J=38 Hz), 62.2, 36.8, 31.4, 24.6, 22.6, 14.1; GCMS: 157, 137, 115, 104, 91.

EXAMPLE 2

Synthesis of S-1-Bromo-1,1-difluoro-non-2-yn-4-ol

R = n-C$_5$H$_{11}$-

To a solution of 2-[1-(3-Bromo-3,3-difluoro-prop-1-ynyl)-hexyloxy]-tetrahydro-pyran (1.08 g, 3.2 mmol) 20 mL methanol, TsOH.H$_2$O (12 mg, 0.069 mmol) was added. After the addition was completed, the reaction mixture was stirred for 12 h and quenched with saturated aq. NaHCO$_3$. The mixture was extracted with ether (20 mL×3) and washed with water (20 mL×2). After drying over Na$_2$SO$_4$ the solvent was removed and the product was purified by silica gel chromatography (DCM:Hexane=1:1) to afford the title compound (0.58 g, 71%) as colorless liquid: yield: 78%. IR (neat): 3320, 2934, 2261, 1223, 1096 cm$^{-1}$. $^1$H NMR (500 MHz, CDCl$_3$) δ 4.49-4.52 (m, 1H), 2.14 (bs, 1H), 1.74-1.77 (m, 2H), 1.45-1.47 (m, 2H), 1.33-1.38 (m, 4H), 0.91 (t, J=6.5 Hz, 3H); $^{19}$F NMR (470 MHz, CDCl$_3$) δ −32.9 (s, 2F); $^{13}$C NMR (125 MHz, CDCl$_3$) δ 101.5 (t, J=288 Hz), 91.5 (t, J=5.8 Hz), 77.3 (t, J=38 Hz), 62.2, 36.8, 31.4, 24.6, 22.6, 14.1; GCMS: 157, 137, 115, 104, 91.

The intermediate 2-[1-(3-Bromo-3,3-difluoro-prop-1-ynyl)-hexyloxy]-tetrahydro-pyran was prepared as follows.
a. S-2-(1-Ethynyl-hexyloxy)-tetrahydropyran. To a solution of S-oct-1-yn-3-ol (900 mg, 7.13 mmol) and 3,4-dihydro-2H-pyran (901 mg, 10.7 mMol) in 5 mL dichloromethane, TsOH.H$_2$O (13 mg, 0.071 mMol) was added. After the addition was completed, the reaction mixture was stirred for 12 h and quenched with saturated aq. NaHCO$_3$. The mixture was extracted with DCM (20 mL×3) and washed with water (20 mL×2). After drying over Na$_2$SO$_4$ the solvent was removed and the product was purified by silica gel chromatography (AcOEt:hexane=1:10) to afford 2-(1-ethynyl-hexyloxy)tetrahydropyran (1.27 g, 85%) as colorless liquid. The product was a mixture of two diastereomers (ratio 1:5.8). Major diastereomer: $^1$H NMR (500 MHz, CDCl$_3$) δ 4.98-4.97 (m, 1H), 4.40-4.43 (m, 1H), 3.79-3.83 (m, 1H), 3.53-3.55 (m, 1H), 2.38 (s, 1H), 1.71-1.84 (m, 4H), 1.44-1.62 (m, 6H), 1.33-1.34 (m, 4H), 0.91 (t, J=6.5 Hz, 3H)

b. 2-[1-(3-Bromo-3,3-difluoro-prop-1-ynyl)-hexyloxy]-tetrahydro-pyran. To a solution of S-2-(1-ethynyl-hexyloxy)tetrahydropyran (1.24 g, 5.9 mmol) in dry THF 30 mL, a 2.5 M hexane solution of n-butyllithium (2.36 mL, 5.9 mmol) was added dropwise at approximately −90° C. (liquid N$_2$/EtOH bath) under an argon atmosphere. After the reaction mixture was stirred for 30 minutes at that temperature, the reaction mixture was cooled to −110° C. (because the solvent along the wall of reaction flask froze at −110° C., it is helpful to maintain good stirring throughout). Cold dibromodifluoromethane (5.5 mL, 60 mmol) was added to the mixture by cannulation. The temperature of the reaction mixture was controlled very carefully during the addition of CF$_2$Br$_2$ using a thermometer immersed in the reaction mixture. The reaction temperature may rise to −90° C. or even higher even if CF$_2$Br$_2$ is introduced slowly. After the addition was completed, the mixture was allowed to warm to −50° C. with stirring during the course of 1 hour and quenched with sat. aq. NH$_4$Cl (50 mL). The aqueous layer was extracted with ether (50 mL) and the organic layer was washed by water (10 mL×3). The organic layer was dried over Na$_2$SO$_4$. After evaporation of the solvent, the product was purified by silica gel chromatography (AcOEt:Hexane=1:10) to afford product (1.5 g, 75%) as colorless liquid. The product is mixture of two diastereomers (ratio 1:9.5). Major diastereomer:

$^1$H NMR (500 MHz, CDCl$_3$) δ 4.88-4.85 (m, 1H), 4.56-4.58 (m, 1H), 3.78-3.81 (m, 1H), 3.55-3.57 (m, 1H), 1.72-1.83 (m, 6H), 1.49-1.64 (m, 4H), 1.33-1.34 (m, 4H), 0.91 (t, J=6.5 Hz, 3H); $^{19}$F NMR (470 MHz, CDCl$_3$) δ −32.9 (s), −32.3 (d, J=9.8 Hz)

EXAMPLE 3

Synthesis of 6-Bromo-6,6-difluoro-2,2-dimethyl-hex-4-yn-3-ol

To a solution of (3-bromo-3,3-difluoro-prop-1-ynyl)-triisopropyl-silane (156 mg, 0.5 mmol) and 2,2-dimethyl-propionaldehyde (52 mg, 0.6 mmol) in THF (5 mL), TBAF (1M, 0.75 mL) was added dropwise at −90° C. After the addition was completed, the reaction mixture was stirred for 0.5 hour and quenched saturated aq. NH$_4$Cl. The mixture was extracted with ether (20 mL×3) and washed with water (20 mL×2). After drying over Na$_2$SO$_4$ the solvent was removed and the product was purified by silica gel chromatography (AcOEt:hexane=1:20) to afford the title compound as a colorless liquid. $^1$H NMR (500 MHz, CDCl$_3$) δ 4.08-4.09 (m, 1H), 1.83 (d, J=6.0 Hz, 1H), 0.965 (s, 9H).

EXAMPLE 4

Synthesis of Representative Compounds of Formula (I)

Using the synthetic processes illustrated above, the following compounds of Formula (I) were prepared. Most compounds were prepared by reaction of TIPS or other silyl protecting group (R', R'', R''' methyl, ethyl, phenyl, iso-propyl, tert-butyl, phenyl) substituted difluoropropargyl bromide with an aldehyde in the presence of fluoride ion (TBAF or a suitable source of fluoride ion). Other compounds were made by direct difluorobromomethylation of functionalized terminal alkynes.

| R$_1$ | R$_2$ | Chemical shift of $^1$H (RCHOH) | Chemical shift of $^{19}$F NMR |
|---|---|---|---|
| 2,2-dimethyl-1-hydroxyprop-1-yl | bromodifluoromethyl | 4.08 | −32.8 |
| 1-hydroxyhept-4-ene-1-yl | bromodifluoromethyl | 4.54 | −33.0 |
| 3-phenyl-1-hydroxyprop-1-yl | bromodifluoromethyl | 5.14 | −32.7 |
| 1-hydroxy-hex-1-yl | bromomethyl | 3.95 | — |
| 1-hydroxy-hex-1-yl | bromodifluoromethyl | 4.49 | −32.9 |
| R-1-hydroxy-hex-1-yl | bromodifluoromethyl | 4.49 | −32.9 |
| S-1-hydroxy-hex-1-yl | bromodifluoromethyl | 4.49 | −32.9 |
| carboxy | bromodifluoromethyl | — | −38.2 |
| 1-bromohex-1-yl | bromodifluoromethyl | 4.52 | −33.5 |
| 1-benzoyloxyhex-1-yl | bromodifluoromethyl | 5.75 | |
| 1-acetoxyhex-1-yl | bromodifluoromethyl | 5.46 | −33.5 |
| 1-phenoxyhex-1-yl | bromodifluoromethyl | | |
| 1-hydroxy-but-1-yl | bromodifluoromethyl | 4.53 | −32.8 |
| 1-hydroxyoct-1-yl | bromodifluoromethyl | 4.52 | −32.9 |
| 1-hydroxy-1-dec-1-yl | bromodifluoromethyl | 4.52 | −32.9 |
| 1-hydroxy-1-dodec-1-yl | bromodifluoromethyl | 4.52 | −32.8 |
| 1-cyclopropyl-1-hydroxymethyl | bromodifluoromethyl | 4.27 | −33.0 |
| 1-cyclohexyl-1-hydroxymethyl | bromodifluoromethyl | 4.31 | −32.7 |
| 1-hydroxy-2,4-hexadiene-1-yl | bromodifluoromethyl | 5.04 | −33.3 |
| 2-ethyl-1-hydroxyhex-1-yl | bromodifluoromethyl | 4.54 | −32.8 |
| 2-methyl-1-hydroxypent-1-yl | bromodifluoromethyl | 4.40 | −32.8 |
| 3-[N-(benzyloxycarbonyl)amino]-1-hydroxyprop-1-yl | bromodifluoromethyl | 4.61 | −33.0 |
| (dioxolane structure) | bromodifluoromethyl | 4.48 / 4.56 | −33.8 / −33.7 |

(Mixture of two isomers)

EXAMPLE 5

The following illustrate representative pharmaceutical dosage forms, containing a compound of Formula (I) ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 10 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |

|  |  |
| --- | --- |
| (iv) Injection 1 (1 mg/ml) | mg/ml |
| 1.0 N Sodium hydroxide solution (pH adjustment to 7.0-7.5) | q.s. |
| Water for injection | q.s. ad 1 mL |

|  |  |
| --- | --- |
| (v) Injection 2 (10 mg/ml) | mg/ml |
| Compound X = (free acid form) | 10.0 |
| Monobasic sodium phosphate | 0.3 |
| Dibasic sodium phosphate | 1.1 |
| Polyethylene glycol 400 | 200.0 |
| 0.1 N Sodium hydroxide solution (pH adjustment to 7.0-7.5) | q.s. |
| Water for injection | q.s. ad 1 mL |

|  |  |
| --- | --- |
| (vi) Aerosol | mg/can |
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of Formula (I):

(I)

wherein:
$R_1$ is $(C_1-C_{20})$alkyl, $(C_2-C_{20})$alkenyl, or $(C_2-C_{20})$alkynyl, which $(C_{1-20})$alkyl, $(C_2-C_{20})$alkenyl, or $(C_2-C_{20})$alkynyl, is substituted with one or more groups independently selected from halo, hydroxy, mercapto, $(C_1-C_{20})$alkoxy, $(C_2-C_{20})$alkenyloxy, $(C_2-C_{20})$alkynyloxy, aryloxy, heteroaryloxy, $(C_3-C_{20})$cycloalkyloxy, heterocyclyloxy, $(C_1-C_{20})$alkylthio, $(C_2-C_{20})$alkenylthio, $(C_2-C_{20})$alkynylthio, carboxy, $(C_2-C_{20})$ alkenyloxycarbonyl, $(C_2-C_{20})$alkynyloxycarbonyl, aryl, heteroaryl, cycloalkyl, heterocyclyl, $NR_aR_b$, $(C_2-C_{20})$alkynoyloxy, and arylcarbonyloxy;
$R_2$ is $CF_2Br$, $CF_2Cl$, $CFBr_2$, $CFCl_2$, $CBr_3$, $CF(R_e)Br$, $CF_2I$, $CF(R_e)I$ or $CCl_3$;
each $R_a$ and $R_b$ is independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, $(C_2-C_{20})$alkynyloxy, or aryl-$(C_1-C_{20})$alkoxycarbonyl; and
$R_e$ is $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy;

wherein each aryl, heteroaryl, heterocyclyl, aryloxy, heteroaryloxy, arylcarbonyloxy or heteroarylcarbonyloxy of $R_1$ is optionally substituted with one or more groups independently selected from halo, hydroxy, nitro, cyano, trifluoromethyl, trifluoromethoxy, mercapto, carboxy, $(C_1-C_{20})$alkyl, $(C_2-C_{20})$alkenyl, $(C_2-C_{20})$alkynyl, $(C_1-C_{20})$alkoxy, $(C_2-C_{20})$alkenyloxy, $(C_2-C_{20})$alkynyloxy, $(C_1-C_{20})$alkylthio, $(C_2-C_{20})$alkenylthio, $(C_2-C_{20})$alkynylthio, $(C_1-C_{20})$alkoxycarbonyl, $(C_2-C_{20})$alkenyloxycarbonyl, $(C_2-C_{20})$alkynyloxycarbonyl, aryl, heteroaryl, aryl$(C_1-C_{20})$alkyl, heteroaryl$(C_1-C_{20})$alkyl, aryl$(C_2-C_2O)$alkenyl, aryl$(C_2-C_{20})$alkynyl, heteroaryl$(C_2-C_{20})$alkenyl, heteroaryl$(C_2-C_{20})$alkynyl, $(C_1-C_{20})$alkanoyloxy, $(C_2-C_{20})$alkenoyloxy, $(C_2-C_{20})$alkynoyloxy;
or a salt thereof;
provided the compound is not 4-bromo-4,4-difluorobut-2-ynoic acid or 1-bromo-1,1-difluoro-non-2-yn-4-ol.

2. The compound of claim 1 wherein:
$R_1$ is $(C_1-C_{20})$alkyl, $(C_2-C_{20})$alkenyl, or $(C_2-C_{20})$alkynyl, which $(C_1-C_{20})$alkyl, $(C_2-C_{20})$alkenyl, or $(C_2-C_{20})$alkynyl, is substituted with one or more groups independently selected from halo, hydroxy, mercapto, $(C_1-C_{20})$alkoxy, $(C_2-C_{20})$alkenyloxy, $(C_2-C_{20})$alkynyloxy, $(C_1-C_{20})$alkylthio, $(C_2-C_{20})$alkenylthio, $(C_2-C_{20})$alkynylthio, carboxy, $(C_2-C_{20})$alkenylcarbonyl, $(C_2-C_{20})$alkynyloxycarbonyl, aryl, heteroaryl, and $NR_aR_b$;
$R_2$ is $CF_2Br$, $CF_2Cl$, $CFBr_2$, $CFCl_2$, $CBr_3$, or $CCl_3$;
each $R_a$ and $R_b$ is independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy; and
$R_e$ is $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy;
wherein each aryl or heteroaryl of $R_1$ is optionally substituted with one or more groups independently selected from halo, hydroxy, nitro, cyano, trifluoromethyl, trifluoromethoxy, mercapto, carboxy, $(C_{1-C20})$alkyl, $(C_2-C_{20})$alkenyl, $(C_2-C_{20})$alkynyl, $(C_1-C_{20})$alkoxy, $(C_2-C_{20})$alkenyloxy, $(C_{2-C20})$alkynyloxy, $(C_1-C_{20})$alkylthio, $(C_2-C_{20})$alkenylthio, $(C_2-C_{20})$alkynylthio, $(C_1-C_{20})$alkoxycarbonyl, $(C_2-C_{20})$alkenyloxycarbonyl, $(C_2-C_{20})$alkynyloxycarbonyl, aryl, heteroaryl, aryl$(C_1-C_{20})$alkyl, heteroaryl$(C_1-C_{20})$alkyl, aryl$(C_2-C_{20})$alkenyl, aryl$(C_2-C_{20})$alkynyl, heteroaryl$(C_2-C_{20})$alkenyl, heteroaryl$(C_2-C_{20})$alkynyl, $(C_1-C_{20})$alkanoyloxy, $(C_2-C_{20})$alkenoyloxy, $(C_2-C_{20})$alkynoyloxy;
or a salt thereof.

3. The compound of claim 1 provided the compound is not 6-bromo-6, 6-difluoro-2-methylhex-4-yn-3-ol.

4. The compound of claim 1 wherein $R_1$ is a $(C_1-C_{20})$alkyl, $(C_2-C_{20})$alkenyl, or $(C_2-C_{20})$alkynyl, which $(C_1-C_{20})$alkyl, $(C_2-C_{20})$alkenyl, or $(C_2-C_{20})$alkynyl is substituted with hydroxy, mercapto, carboxy or $NR_aR_b$.

5. The compound of claim 1 wherein $R_1$ is a $(C_1-C_{20})$alkyl, $(C_2-C_{20})$alkenyl, or $(C_2-C_{20})$alkynyl, which $(C_1-C_{20})$alkyl, $(C_2-C_{20})$alkenyl, or $(C_2-C_{20})$alkynyl is substituted with hydroxy.

6. The compound of claim 1 wherein $R_1$ is a $(C_1-C_{20})$alkyl, $(C_2-C_{20})$alkenyl, or $(C_2-C_{20})$alkynyl, which $(C_1-C_{20})$ alkyl, $(C_2-C_{20})$alkenyl, or $(C_2-C_{20})$alkynyl is substituted on the carbon adjacent to the triple bond in Formula (I) with hydroxy.

7. The compound of claim 1 wherein $R_1$ is a $(C_5-C_{10})$alkyl, $(C_2-C_{10})$alkenyl, or $(C_2-C_{10})$alkynyl that is substituted with hydroxy, mercapto, carboxy or $NR_aR_b$.

8. A compound of Formula (I):

$$R_1 \mathrel{\equiv\!\equiv\!\equiv} R_2 \quad (I)$$

or a salt thereof, wherein $R_1$ is a $(C_5$-$C_{10})$alkyl, $(C_2$-$C_{10})$alkenyl, or $(C_2$-$C_{10})$alkynyl that is substituted with hydroxy;
$R_2$ is $CF_2Br$, $CFHBr$, $CF_2Cl$, $CFHCl$, $CFBr_2$, $CFCl_2$, $CBr_3$, $C(R_c)(R_d)Br$, $C(R_c)(R_d)Cl$, $CF(R_e)Br$, $CF_2I$, $CFHI$, $C(R_c)(R_d)I$, $CF(R_e)I$ or $CCl_3$;
each $R_c$ and $R_d$ is independently H, $(C_1$-$C_{20})$alkyl, $(C_1$-$C_{20})$alkanoyl, $(C_2$-$C_{20})$alkenylcarbonyl, $(C_2$-$C_{20})$alkynylcarbonyl, $(C_1$-$C_{20})$alkoxy, $(C_2$-$C_{20})$alkenyloxy, or $(C_2$-$C_{20})$alkynyloxy; and
$R_e$ is $(C_1$-$C_{20})$alkyl, $(C_1$-$C_{20})$alkanoyl, $(C_2$-$C_{20})$alkenylcarbonyl, $(C_2$-$C_{20})$alkynylcarbonyl, $(C_1$-$C_{20})$alkoxy, $(C_{,2}$-$C_{20})$alkenyloxy, or $(C_2$-$C_{20})$alkynyloxy.

9. The compound of claim 8 wherein $R_1$ is a $(C_5$-$C_{10})$alkyl, $(C_2$-$C_{10})$alkenyl, or $(C_2$-$C_{10})$alkynyl that is substituted on the carbon adjacent to the triple bond in Formula (I) with hydroxy.

10. The compound of claim 1 wherein $R_1$ is a $(C_5$-$C_{10})$alkyl that is substituted with hydroxy, mercapto, carboxy or $NR_aR_b$.

11. The compound of claim 8 wherein $R_1$ is a $(C_5$-$C_{10})$alkyl that is substituted with hydroxy.

12. The compound of claim 8 wherein $R_1$ is a $(C_5$-$C_{10})$alkyl that is substituted on the carbon adjacent to the trip bond in Formula (I) with hydroxyl.

13. The compound of claim 1 wherein $R_1$ is $(C_1$-$C_{20})$alkyl, $(C_2$-$C_{20})$alkenyl, or $(C_2$-$C_{20})$alkynyl, which $(C_1$-$C_{20})$alkyl, $(C_2$-$C_{20})$alkenyl, or $(C_2$-$C_{20})$alkynyl is substituted with $(C_1$-$C_{20})$alkanoyloxy.

14. The compound of claim 1 wherein $R_1$ is a $(C_5$-$C_{10})$alkyl that is substituted on the carbon adjacent to the triple bond in Formula (I) with $(C_1$-$C_{20})$alkanoyloxy.

15. The compound of claim 1 wherein $R_1$ is 1-hydroxyhexane, 1-hydroxy-2, 2-dimethylpropane, 1-acetoxyhexane or cis-1-hydroxy-3-hexane.

16. The compound of claim 1 wherein $R_1$ is a $(C_5$-$C_{10})$alkyl that is substituted on the carbon adjacent to the triple bond in Formula (I) with acetoxy.

17. The compound of claim 1 wherein $R_2$ is $CF_2Br$, or $CF_2Cl$.

18. The compound of claim 1 wherein $R_2$ is $CF_2Br$.

19. The compound of claim 1 wherein the compound of formula (I) is a compound of formula (II):

$$\begin{array}{c} R_3 \\ \phantom{x} \diagdown \\ \phantom{xx}\mathrel{\equiv\!\equiv\!\equiv}\!-CF_2Br \\ \phantom{x} \diagup \\ R_4 \end{array} \quad (II)$$

wherein: $R_3$ is hydroxy, mercapto, chloro, bromo, methylthio, ethylthio, methoxy, ethoxy, acetylamino, $(C_1$-$C_{20})$alkanoyloxy, arylcarbonyloxy, aryloxy; and $R_4$ is $(C_4$-$C_{10})$alkyl, $(C_2$-$C_{10})$alkenyl, or $(C_2$-$C_{10})$alkynyl, which $(C_4$-$C_{10})$alkyl, $(C_2$-$C_{10})$alkenyl, or $(C_2$-$C_{10})$alkynyl is optionally substituted with one or more groups independently selected from halo, hydroxy, mercapto, $(C_1$-$C_{10})$alkoxy, $(C_1$-$C_{10})$alkylthio, carboxy, $(C_1$-$C_{10})$alkoxycarbonyl, aryl, heteroaryl, and $NR_aR_b$.

20. The compound of claim 19 wherein: $R_3$ is hydroxy, mercapto, chloro, bromo, methylthio, ethylthio, methoxy, ethoxy, or acetylamino; and $R_4$ is $(C_4$-$C_{10})$alkyl, $(C_2$-$C_{10})$alkenyl, or $(C_2$-$C_{10})$alkynyl, which $(C_4$-$C_{10})$alkyl, $(C_2$-$C_{10})$alkenyl, or $(C_2$-$C_{10})$alkynyl is optionally substituted with one or more groups independently selected from halo, hydroxy, mercapto, $(C_1$-$C_{10})$alkoxy, $(C_1$-$C_{10})$alkylthio, carboxy, $(C_1$-$C_{10})$alkoxycarbonyl, aryl, heteroaryl, and $NR_aR_b$.

21. The compound of claim 19 wherein $R_4$ is $(C_4$-$C_{10})$alkyl that is optionally substituted with one or more groups independently selected from halo, hydroxy, mercapto, $((C_1$-$C_{10})$alkoxy, $(C_1$-$C_{10})$alkylthio, carboxy, $(C_1$-$C_{10})$alkoxycarbonyl, aryl heteroaryl, and $NR_aR_b$.

22. The compound of claim 19 wherein $R_4$ is $(C_4$-$C_{10})$alkyl that is optionally substituted with one or more groups independently selected from halo, hydroxy, mercapto, carboxy, $(C_1$-$C_{10})$alkoxycarbonyl, and $NR_aR_b$.

23. The compound of claim 19 wherein $R_4$ is $(C_4$-$C_{10})$alkyl.

24. The compound of claim 19 wherein $R4$ is $(C_4$-$C_6)$alkyl.

25. The compound 1-bromo-1,1,difluoro-4-hydroxy-5,5-dimethyl-2-hexyne, or a salt thereof.

26. The compound

[chemical structure]

or a salt thereof.

27. A pharmaceutical composition comprising a compound of Formula (I):

$$R_1 \mathrel{\equiv\!\equiv\!\equiv} R_2 \quad (I)$$

wherein:
$R_1$ is $(C_1$-$C_{20})$alkyl, $(C_2$-$C_{20})$alkenyl, or $(C_2$-$C_{20})$alkynyl, which $(C_1$-$C_{20})$alkyl, $(C_2$-$C_{20})$alkenyl, or $(C_2$-$C_{20})$alkynyl, is substituted with one or more groups independently selected from halo, hydroxy, mercapto, $(C_1$-$C_{20})$alkoxy, $(C_2$-$C_{20})$alkenyloxy, $(C_2$-$C_{20})$alkynyloxy, aryloxy, heteroaryloxy, $(C_3$-$C_{20})$cycloalkyloxy, heterocyclyloxy, $(C_1$-$C_{20})$alkylthio, $(C_2$-$C_{20})$alkenylthio, $(C_2$-$C_{20})$alkynylthio, carboxy, $(C_2$-$C_{20})$alkenyloxycarbonyl, $(C_2$-$C_{20})$alkynyloxycarbonyl, aryl, heteroaryl, cycloalkyl, heterocyclyl, $NR_aR_b$, $(C_2$-$C_{20})$alkynoyloxy, and arylcarbonyloxy;
$R_2$ is $CF_2Br$, $CF_2Cl$, $CFBR_2$, $CFCl_2$, $CBr_3$, $CF(R_e)Br$, $CF_2I$, $CF(R_e)I$, or $CCl_3$;
each $R_a$ and $R_b$ is independently H, $(C_1$-$C_{20})$alkyl, $(C_1$-$C_{20})$alkanoyl, $(C_2$-$C_{20})$alkenylcarbonyl, $(C_2$-$C_{20})$alkynylcarbonyl, $(C_1$-$C_{20})$alkoxy, $(C_2$-$C_{20})$alkenyloxy, $(C_2$-$C_{20})$alkynloxy, or aryl-$(C_1$-$C_{20})$alkoxycarbonyl; and
$R_e$ is $(C_1$-$C_{20})$alkyl, $(C_1$-$C_{20})$alkanoyl, $(C_2$-$C_{20})$alkenylcarbonyl, $(C_2$-$C_{20})$alkynylcarbonyl, $(C_1$-$C_{20})$alkoxy, $(C_2$-$C_{20})$alkenyloxy, or $(C_2$-$C_{20})$ alkynyloxy;

wherein each aryl, heteroaryl, heterocyclyl, aryloxy, or heteroaryloxy, arylcarbonyloxy or heteroarylcarbonyloxy or R1 is optionally substituted with one or more goups independently selected from halo, hydroxy, nitro, cyano, trifluoromethyl, trifluoromethoxy, mercapto, carboxy, $(C_1-C_{20})$alkyl, $(C_2-C_{20})$alkenyl, $(C_2-C_{20})$alkynyl, $(C_1-C_{20})$alkoxy, $(C_2-C_{20})$alkenyloxy, $(C_2-C_{20})$alkynyloxy, $(C_1-C_{20})$ alkylthio, $(C_2-C_{20})$alkenylthio, $(C_2-C_{20})$alkynylthio, $(C_1-C_{20})$alkoxycarbonyl, $(C_2-C_{20})$alkenyloxycarbonyl, $(C_2-C_{20})$alkynylcarbonyl, aryl, heteroaryl, aryl$(C_1-C_{20})$alkyl, heteroaryl$(C_1-C_{20})$alkyl, aryl$(C_2-C_{20})$alkenyl, aryl$(C_2-C_{20})$alkynyl, heteroaryl$(C_2-C_{20})$alkenyl, heteroaryl$(C_2-C_{20})$alkynyl, $(C_1-C_{20})$alkenoyloxy, $(C_2-C_{20})$alkynyloxy;

or a pharmaceutically acceptable salt thereof;

and a pharmaceutically acceptable carrier; provided the compound is not 4-bromo-4,4-difluorobut-2-ynoic acid or 1-bromo-1,1-difluoro-non-2-yn-4-ol.

28. The compound of claim 1, wherein $R_1$ is 1-hydroxyhexane, 1-hydroxyoctane, 1-hydroxydecane, 1-acetoxyhexane, cis-1-hydroxy-3-hexene, or cis-1-hydroxy-4-heptane; and R2 is CF2Br.

29. The compound of claim 8, wherein the $(C_5-C_{10})$alkyl, $(C_2-C_{10})$alkenyl, or $(C_2-C_{10})$alkynyl is further substituted with a hydroxy.

30. The compound of claim 8, wherein the $(C_5-C_{10})$alkyl, $(C_2-C_{10})$alkenyl, or $(C_2-C_{10})$alkynyl is further substituted with a carboxy.

31. A method for treating cancer in an animal in need thereof, wherein the cancer is selected from the group consisting of breast cancer, prostate cancer, colon cancer and brain tumor, which method comprises administering a treatment effective amount of a compound of claim 8, or a pharmaceutically acceptable salt thereof, to the animal.

32. A method for inhibiting DNA methyltransferase activity in an animal, which method comprises administering a compound of claim 8, or a pharmaceutically acceptable salt thereof, to the animal.

33. A method for treating cancer in an animal in need thereof, wherein the cancer is selected from the group consisting of breast cancer, prostate cancer, colon cancer and brain tumor, which method comprises administering a treatment effective amount of a compound of claim 19, or a pharmaceutically acceptable salt thereof, to the animal.

34. A method for inhibiting DNA methyltransferase activity in an animal, which method comprises administering a compound of claim 19, or a pharmaceutically acceptable salt thereof, to the animal.

35. A method for treating cancer in an animal in need thereof, wherein the cancer is selected from the group consisting of breast cancer, prostate cancer, colon cancer and brain tumor, which method comprises administering a treatment effective amount of a compound of claim 26, or a pharmaceutically acceptable salt thereof, to the animal.

36. A method for inhibiting DNA methyltransferase activity in an animal, which method comprises administering a compound of claim 26, or a pharmaceutically acceptable salt thereof, to the animal.

* * * * *

UNITED STATES PATENT AND TRADEMARK OFFICE
CERTIFICATE OF CORRECTION

PATENT NO. : 8,207,381 B2
APPLICATION NO. : 12/027154
DATED : June 26, 2012
INVENTOR(S) : Hammond et al.

Figure 2A:
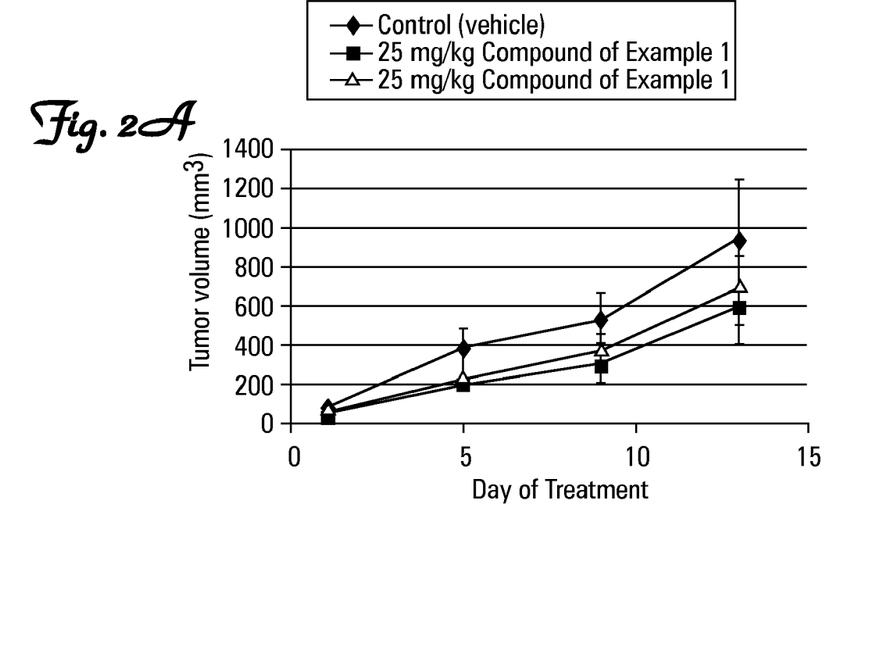
FIG. 2. Shows the in vivo effects of the compound of Example 1 from Test F. Female nude mice with established A549 xenografts (n=7 per group) received injections (i.p.) of the compound of Example 1 or vehicle up to 30 times with no evidence of toxicity. (A) Tumor growth appeared to be reduced in mice treated with the compound of Example 1, but the effect was not statistically significant ($p \geqq 0.13$). (B) IACUC protocol mandated that mice with ulcerated/necrotic tumors had to be euthanized, but the tumors in mice that had necrosis were substantially smaller than control tumors. The table shows data for the three treated mice euthanized before the end of the experiment due to tumor necrosis. Compare with the mean ±SE in the control group.

It is certified that error appears in the above-identified patent and that said Letters Patent is hereby corrected as shown below:

In the Drawings:

Sheet 4, FIG. 2A, "25 mg/kg" to the right of the open triangle symbol, should read --50 mg/kg--.

Figure 2B:
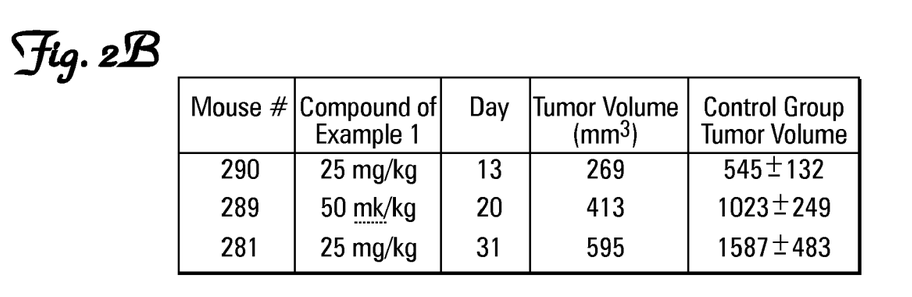

Sheet 4, FIG. 2B, "50 mk/kg" should read --50 mg/kg--.

In the Specification:

Column 12, lines 46-47, "(see Methods Mol Biol 1998, 79, 79-83)." should read --(see Morgan, "Tetrazolium (MTT) Assay for Cellular Viability and Activity" Methods in Molecular Biology (1998) Vol. 79, pp. 179-183).--; lines 55-56, "by Carcinogenesis, 2006, 27, 269-77 can" should read --by Lee et al. 2006 (Lee et al., "Inhibition of DNA methylation by caffeic acid and chlorogenic acid, two common catechol-containing coffee polyphenols" Carcinogenesis (Feb. 2006) Vol. 27, No. 2, pp. 269-277) can--.

Column 19, line 49, "which $(C_1 - _{20})$alkyl," should read --which $(C_1 - C_{20})$alkyl,--.

Column 20, line 13, "$C_2$o)alkenyl," should read --$C_{20}$)alkenyl,--; line 15, "$(C_2-C_{20})$alkenoyloxy," should read --$(C_2-C_{20})$alkenoyloxy, and--; line 40, "$(C_{1-C20})$alkyl," should read --$(C_1-C_{20})$alkyl,--; line 42, "$(C_{2-C20})$alkynyloxy," should read --$(C_2-C_{20})$alkynyloxy,--; line 49, "alkenoyloxy, $(C_2-C_{20})$alkynoyloxy;" should read --alkenoyloxy, and $(C_2-C_{20})$alkynoyloxy;--; line 52, "6-bromo-6, 6-difluoro-2" should read --6-bromo-6,6-difluoro-2--.

Column 21, line 20, "$(C_{,2}-C_{20})$alkenyloxy," should read --$(C_2-C_{20})$alkenyloxy,--; line 31, "trip bond" should read --triple bond--; line 41, "1-hydroxy-2, 2-dimethylpropane," should read --1-hydroxy-2,2-dimethylpropane,--.

Column 22, line 12, "aryl heteroaryl," should read --aryl, heteroaryl,--; line 19, "R4 is $(C_4-C_6)$alkyl."

Signed and Sealed this
Eleventh Day of March, 2014

Michelle K. Lee
*Deputy Director of the United States Patent and Trademark Office*

CERTIFICATE OF CORRECTION (continued)
U.S. Pat. No. 8,207,381 B2 should read --$R_4$ is $(C_4-C_6)$alkyl.--; line 20, "1-bromo-1,1,difluoro-4-hydroxy-5," should read --1-bromo-1,1-difluoro-4-hydroxy-5,--; line 55, "$(C_2\ C_{20})$alkenyloxycarbonyl," should read --$(C_2-C_{20})$alkenyloxycarbonyl,--; line 59, "$CFBR_2$" should read --$CFBr_2$--.

Column 23, line 1, "aryloxy, or" should read --aryloxy,--; line 3, "loxy or R1" should read --loxy of $R_1$--; line 14, "alkenoyloxy, $(C_2-C_{20})$alkynyloxy;" should read --alkenoyloxy, and $(C_2-C_{20})$alkynyloxy;--; line 23, "R2 is CF2Br." should read --$R_2$ is $CF_2Br$.--.